United States Patent [19]
Ford

[11] Patent Number: 5,746,595
[45] Date of Patent: May 5, 1998

[54] TOOTHBRUSH

[76] Inventor: Frank E. Ford, 4416 Willow Bend Dr., Arlington, Tex. 76017

[21] Appl. No.: 597,610

[22] Filed: Feb. 6, 1996

[51] Int. Cl.⁶ .................................................. A61G 17/02
[52] U.S. Cl. .......................... 433/80; 601/162; 601/165; 401/289
[58] Field of Search ............................ 433/80, 81, 216; 15/167.1; 401/268, 270, 271, 280, 281, 286, 287, 289; 601/160, 162–165

[56] References Cited

U.S. PATENT DOCUMENTS

| | | | |
|---|---|---|---|
| 913,184 | 2/1909 | Alexander | 401/289 |
| 3,039,123 | 6/1962 | Brucker et al. | 601/162 |
| 3,214,775 | 11/1965 | Murov et al. | 601/163 |
| 3,690,314 | 9/1972 | Trupp et al. | 601/165 |
| 3,910,265 | 10/1975 | Coleman | 601/160 |
| 4,111,193 | 9/1978 | Jousson | 601/162 |
| 4,175,879 | 11/1979 | Molinari | 401/287 |
| 4,257,433 | 3/1981 | Kwan | 601/162 |
| 4,303,064 | 12/1981 | Buffer . | |
| 4,903,688 | 2/1990 | Bibby et al. . | |
| 4,979,503 | 12/1990 | Chernack | 601/165 |
| 5,095,893 | 3/1992 | Rawden | 601/165 |
| 5,304,010 | 4/1994 | Hsing-San | 401/289 |
| 5,484,281 | 1/1996 | Renow et al. | 601/165 |

FOREIGN PATENT DOCUMENTS

| | | | |
|---|---|---|---|
| 97015 | 12/1983 | European Pat. Off. | 601/162 |
| 2221240 | 11/1973 | Germany | 601/162 |
| 2842829 | 4/1980 | Germany | 433/80 |

*Primary Examiner*—Ralph A. Lewis
*Attorney, Agent, or Firm*—Joseph N. Breaux

[57] ABSTRACT

A toothbrush connectable to a pressurized source of water for expelling a stream of pulsating water from the brush head thereof is provided. The toothbrush, includes: a body having a conduit therein in fluid communication between a water inlet and a plurality of holes formed in the brush head of the body, a flexible hose having a first end connected to the water inlet and a second end connectable to a pressurized source of water and a pulsatile mechanism in operational connection with the conduit for transforming the flow of water therethrough the conduit into a pulsating stream of water expelled from the holes.

10 Claims, 1 Drawing Sheet

TOOTHBRUSH

TECHNICAL FIELD

The present invention relates to devices and methods for cleaning the teeth and between the teeth and gums of a user and more particularly to devices and methods for cleaning the teeth and between the teeth and gums of a user that have a brush head capable of providing a pulsatile stream of water.

BACKGROUND ART

The existing tools for cleaning teeth comprise a wide range of toothbrushes varying in size, shape and bristle rigidity. These devices while effective in cleaning the teeth of the user are deficient in the area of cleaning between the teeth and gums of the user. Failure to adequately clean between the teeth and gums is known to cause periodontal disease.

Devices from dental floss to integrated irrigation systems have been developed for cleaning between the teeth and gums. Some of these devices provide a pulsating stream of water that may be used in addition to brushing. However, these devices are expensive and require an electrical connection. Further, these devices are bulky, taking up needed counter space and making them impractical for travel. It would be a benefit, therefore, to have an inexpensive, compact and lightweight device for brushing the teeth and capable of providing a pulsating stream of water. It would be a further benefit to have a device that is easily connected to and removed from a pressurized source of water such as a home water faucet. It would be a still further benefit to have a device that does not require any electrical connections.

GENERAL SUMMARY DISCUSSION OF INVENTION

It is thus an object of the invention to provide a toothbrush that has bristles and a pulsating stream of water for cleaning the teeth and between the teeth and gums of a user.

It is a further object of the invention to provide a toothbrush that is connectable to a pressurized source of water.

It is a still further object of the invention to provide a toothbrush that is inexpensive, compact and lightweight.

It is a still further object of the invention to provide a toothbrush that does not require any electrical connections.

Accordingly, a toothbrush connectable to a pressurized source of water for expelling a stream of pulsating water from the brush head thereof is provided. The toothbrush, includes: a body, a flexible hose and a pulsatile mechanism.

The body of the toothbrush has a handle and a brush head constructed of a durable plastic. A conduit is formed by the body in fluid communication between holes formed in the brush head and a water inlet formed in the handle. The brush head also has rows of bristles extending therefrom for brushing the teeth. The holes are located between the rows of bristles. Various combinations of number of holes and diameters of the holes may be utilized to employ various patterns of pulsating water expelled therefrom.

The water inlet may be formed by the rearward end of the handle. The water inlet may be formed between the rearward end of the handle and the brush head. The rearward portion of the handle may be adapted for connecting to a mechanical vibrating device for using the toothbrush in an electric toothbrush configuration.

The flexible hose has a first end connected to the water inlet and a second connector end adapted for connecting to a pressurized source of water. When the pressurized source of water is a water faucet, the second connector end may be a threaded coupling, a break over type clamp, a ratchet type clamp or a flexible fitting for disposing the faucet therein and gripping it.

The pulsatile mechanism is in operational connection with the conduit for transforming the flow of the water through the conduit into a pulsating stream of water expelled from the holes. The pulsatile mechanism may be connectable to the body of the toothbrush or to the flexible hose. Preferably, the mechanism is connected to the handle.

When the pulsatile mechanism is connected to the body of the toothbrush the mechanism includes a paisley shaped water wheel having a rounded section and a concave section. The paisley shaped water wheel is rotatably mounted on shaft within the handle so that a portion of the water wheel extends into the conduit. The water wheel is sized so that flow of water is substantially blocked when the rounded section of the water wheel is disposed within the conduit. The shaft extends a shoe end from the paisley shaped water wheel.

The mechanism further includes a braking mechanism having a circular pad end and a control end connected by a threaded rod member. The rod member is threadedly disposed through the handle so that the control end is located exterior of the handle and so that the circular pad end is concentrically aligned with the shoe end of the paisley shaped water wheel in a manner such that the braking mechanism is functionally connected to the paisley shaped water wheel. The control end may be rotated in a first direction urging the pad end against the shoe end to slow the rotation of the water wheel and the rate of pulsation of the water. The control end may also be rotated in a second direction urging the pad end away from the shoe end increasing the rate of pulsation of the water. Preferably, the pad end is formed of nylon or has a nylon surface for increasing the friction between the pad end and the shoe end when in contact.

The pulsatile mechanism may also include a plurality of paddles extending from the perimeter of the water wheel to facilitate the rotation of the water wheel as water flows through the conduit. The paddles may be rigid or flexible. Preferably, the paddles are semi-flexible to permit them to bend when contacting the sides of the conduit or mounting facility while rotating.

In another embodiment the pulsatile mechanism is connected in fluid communication with the water path through the flexible hose. In this embodiment the mechanism would be constructed in the manner herebefore described with the exception the mechanism would be mounted within a housing as opposed to the toothbrush handle.

The toothbrush may also include a control valve for controlling the rate of flow of water through the toothbrush. The control valve may be mounted in fluid communication with the flow path of the water through either the conduit or the flexible hose. The control valve may be any valve known in the art which may operated between a full closed position and a full open position for providing a range of flow rates through the toothbrush. Preferably, the control valve is a ball valve. More preferably, the control valve is a butterfly valve.

BRIEF DESCRIPTION OF THE DRAWINGS

For a further understanding of the nature and objects of the present invention, reference should be had to the following detailed description, taken in conjunction with the accompanying drawings, in which like elements are given the same or analogous reference numbers and wherein.

EXEMPLARY MODE FOR CARRYING OUT THE INVENTION

Figure 1:
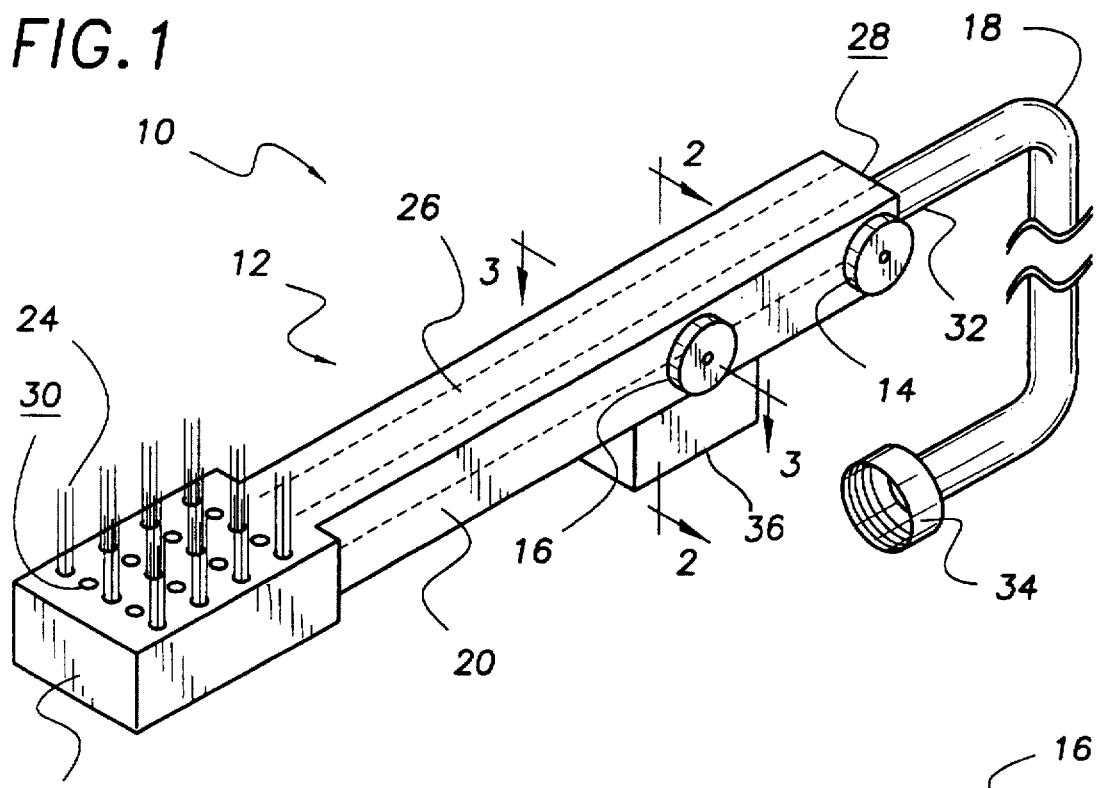
FIG. 1 is a perspective view of an exemplary embodiment of the toothbrush of the present invention.

FIG. 1 is a perspective view of an exemplary embodiment of the toothbrush of the present invention generally designated by the numeral 10. In this embodiment, toothbrush 10 is connectable to a common household water faucet as a source of pressurized water. Toothbrush 10 includes a body 12, a control valve 14, a pulsatile mechanism 16 and a flexible hose 18.

Body 12 has an elongated handle 20 of sufficient size to be hand held and a brush head 22 having bristles 24 extending therefrom. A conduit 26, indicated by hidden lines, is formed within body 12 in fluid communication between a water inlet 28 formed by the rearward end of handle 20 and a plurality of holes 30 formed by brush head 22.

Flexible hose 18 has a first end 32 and a second connector end 34. First end 32 is fluidly connected to water inlet 28. Second connector end 34 is an internally threaded coupling connectable to a standard bathroom water faucet (not shown) for providing water to body 12.

Control valve 14 is a butterfly valve operationally connected to body 12 within conduit 26 for controlling the flow of water to therethrough. Valve 14 is movable from a full open position to a full close position. Valve 14 may be operated between the full open and full close positions to regulate the flow of water through body 12 and holes 30.

Pulsatile mechanism 16 is in operational connection with conduit 26 to transform the flow of water through conduit 26 into a pulsating flow. Pulsatile mechanism 16 is connected within handle 20 and within extension 36 formed by handle 20.

Figure 2:
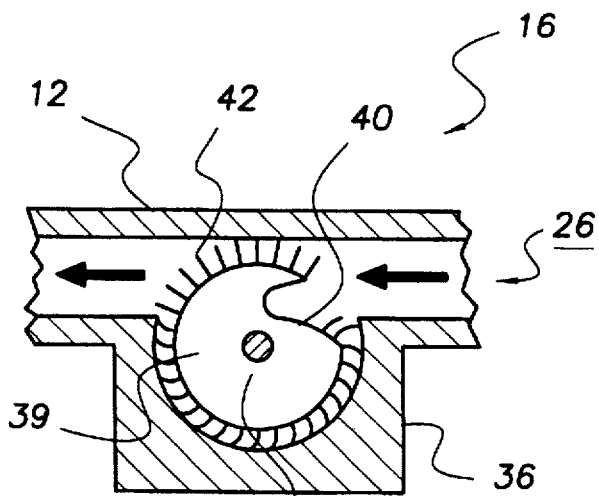
FIG. 2 is a cross-sectional view of the pulsatile mechanism of the toothbrush, along the line 2—2 of FIG. 1.

FIG. 2 is a cross-sectional view of pulsatile mechanism 16 along the line 2—2 of FIG. 1. FIG. 2 shows the paisley shaped, water wheel 38. Paisley shaped wheel 38 is a substantially circular member having a rounded section 39 and a concave section 40 formed along a portion of its edge. Wheel 38 is rotatably mounted within handle 20 so that approximately one-half of wheel 38 extends into conduit 26, the remaining portion extending into extension 36 of handle 20. Wheel 38 is sized to substantially block the flow of water through conduit 26 when rounded section 39 is located therein. Paddles 42 extend from substantially the entire perimeter of wheel 38, so that as water flows through conduit 26 in the direction shown by the arrows wheel 38 rotates.

Figure 3:
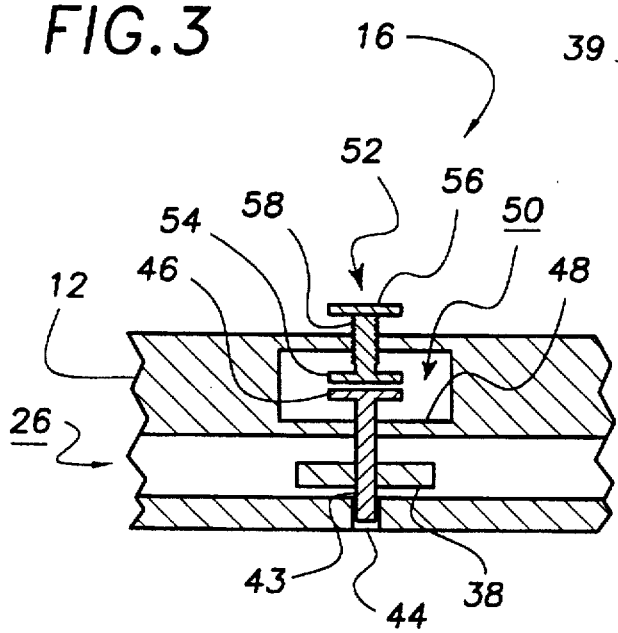
FIG. 3 is a cross-sectional view of the pulsatile mechanism of the toothbrush, along the line 3—3 of FIG. 1.

FIG. 3 is a cross-sectional view of pulsatile mechanism 16 along the line 3—3 of FIG. 1. Paisley shaped wheel 38 within rotatably mounted in conduit 26 by a shaft 43. Shaft 43 has a first shaft end 44 rotatably mounted to handle 20 and a shoe end 46. Shoe end 46 is a circular member. As shown, a portion of shaft 43 extends through a partition 48, locating shoe end 46 in a cavity 50 formed by handle 20. Partition 48 prevents water from flowing around paisley shaped wheel 38.

Pulsatile mechanism 16 includes a braking mechanism 52 having a circular pad end 54 and a control end 56 connected by a threaded rod member 58 for controlling the rotational speed of wheel 38. In this embodiment, pad end 54 is constructed of a rigid nylon material. Braking mechanism 52 is functionally connected to water wheel 38 by concentrically aligning pad end 54 with shoe end 46 of shaft 43 and threadedly disposing rod member 58 through handle 20 with control end 56 located exterior of handle 20. "Functionally connected" is herein defined to mean that by rotating control end 56 in a first direction pad end 54 is urged against shoe end 46 increasing friction therebetween slowing the rotational speed of wheel 38 as water flows through conduit 26, and by rotating control end 56 in a second direction pad end 54 is urged away from shoe end 46 decreasing the friction therebetween, thus allowing the rotational speed of wheel 38 to increase.

Use of toothbrush 10 is now described with reference to FIGS. 1 through 3. Second connector end 34 of hose 18 is threaded onto a water faucet. Control valve 14 is moved to a full closed position and the water faucet is turned on allowing pressurized water to flow through hose 18 into conduit 26 and expelled through holes 30 formed in the brush head 22 of body 12. Brush head 22 is inserted into the user's mouth and operating valve 14 between the full open position and the full closed position regulating the flow of water through body 12 while brushing the teeth.

A pulsating flow of water is created by pulsatile mechanism 16. As water flows through conduit 26 the water contacts paddles 42, rotating paisley shaped water wheel 38. As rounded section 39 of wheel 38 rotates through conduit 26 the path of the water is substantially blocked limiting the flow of water therethrough. As the concave section 40 rotates through conduit 26 the path of the water is cleared allowing a pulse of water to pass. The rate of the pulsation of the water can be decreased by rotating control end 56 of braking mechanism 52 in a first direction urging pad end 54 against shoe end 46 of shaft 43 decreasing the rotational speed of wheel 38. The rate of pulsation may be increased by rotating control end 56 in a second direction urging pad end 56 away from shoe end 46, thus decreasing the friction therebetween, allowing the rotational speed of wheel 38 to increase. With toothbrush 10 operating, a user may clean his teeth and between the teeth and gums using both bristles 24 and the pulsating stream of water expelled from holes 30. After cleaning inside the mouth control valve 14 is moved to the full closed position, brush head 22 is removed from the mouth, the water faucet is turned off and second connector end 34 is disconnected from the water faucet.

It can be seen from the preceding description that a method and device for cleaning the teeth and between the teeth and gums of a user which has bristles and a pulsating stream of water, that is connectable to a pressurized source of water, inexpensive, compact and lightweight, and that does not require any electrical connections has been provided.

It is noted that the embodiment of the toothbrush described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A toothbrush comprising:
   a body having a handle and a brush head, said body forming a conduit therein in fluid connection between a water inlet formed by said handle and a plurality of holes formed by said brush head;

a flexible hose having a first end connected to said water inlet and a second connector end connectable to a source of pressurized water; and a pulsatile mechanism in operational connection with said conduit for transforming the flow of water through said conduit into a pulsating stream of water;

said pulsatile mechanism including:

a paisley shaped water wheel having a rounded section and a concave section, said paisley shaped water wheel being rotatably mounted within said handle with a portion of said paisley shaped water wheel extending into said conduit;

a shaft extending from said paisley shaped water wheel, said shaft having a shoe end; and a braking mechanism having a circular pad end and a control end connected by a threaded rod member, said rod member being threadedly disposed through said handle with said control end located exterior of said handle and said circular pad end being concentrically aligned with said shoe end of said paisley shaped water wheel in a manner such that said braking mechanism is functionally connected to said paisley shaped water wheel.

2. The toothbrush of claim 1, wherein:

said paisley shaped water wheel is rotatably mounted within said handle so that when said rounded section is disposed within said conduit the flow of water therethrough is substantially blocked.

3. The toothbrush of claim 2, wherein:

said pulsatile mechanism further includes:

a plurality of paddles extending from a perimeter of said paisley shaped water wheel.

4. The toothbrush of claim 1, wherein:

said pulsatile mechanism further includes:

a plurality of paddles extending from a perimeter of said paisley shaped water wheel.

5. The toothbrush of claim 4, wherein:

a control valve operationally connected within said conduit for controlling the flow of water therethrough.

6. The toothbrush of claim 1, wherein:

said pad end of said shaft is nylon.

7. The toothbrush of claim 1, further including:

a control valve operationally connected within said conduit for controlling the flow of water therethrough.

8. A toothbrush comprising:

a body having a handle and a brush head having bristles extending therefrom, said body forming a conduit therein in fluid connection between a water inlet formed by said handle and a plurality of holes formed by said brush head;

a flexible hose having a first end connected to said water inlet and a second connector end connectable to a source of pressurized water;

a pulsatile mechanism in operational connection with said conduit for transforming the flow of water through said conduit into a pulsating stream of water, said pulsatile mechanism comprising: a paisley shaped water wheel having a rounded section and a concave section, said paisley shaped water wheel being rotatably mounted within said handle with a portion of said paisley shaped water wheel extending into said conduit; a shaft extending from said paisley shaped water wheel, said shaft having a shoe end; and a braking mechanism having a circular pad end and a control end connected by a threaded rod member, said rod member being threadedly disposed through said handle with said control end located exterior of said handle and said circular pad end being concentrically aligned with said shoe end of said paisley shaped water wheel in a manner such that said braking mechanism is functionally connected to said paisley shaped water wheel;

a plurality of paddles extending from a perimeter of said paisley shaped water wheel; and a control valve operationally connected within said conduit for controlling the flow of water therethrough.

9. The toothbrush of claim 8, wherein:

said pad end of said shaft is nylon.

10. A method of cleaning the teeth and between the teeth and gums of a user, comprising the steps of:

providing a toothbrush, said toothbrush comprising: a body having a handle and a brush head having bristles extending therefrom, said body forming a conduit therein in fluid connection between a water inlet formed by said handle and a plurality of holes formed by said brush head; a flexible hose having a first end connected to said water inlet and a second connector end connectable to a source of pressurized water; a control valve operationally connected within said conduit for controlling the flow of water therethrough; and a pulsatile mechanism in operational connection with said conduit for transforming the flow of water through said conduit into a pulsating stream of water, said pulsatile mechanism comprising: a paisley shaped water wheel having a rounded section and a concave section, said paisley shaped water wheel being rotatably mounted within said handle with a portion of said paisley shaped water wheel extending into said conduit; a shaft extending from said paisley shaped water wheel, said shaft having a shoe end; a braking mechanism having a circular pad end and a control end connected by a threaded rod member, said rod member being threadedly disposed through said handle with said control end located exterior of said handle and said circular pad end being concentrically aligned with said shoe end of said paisley shaped water wheel in a manner such that said braking mechanism is functionally connected to said paisley shaped water wheel; and a plurality of paddles extending from a perimeter of said paisley shaped water wheel;

connecting said second connector end of said flexible hose to a water faucet;

moving said control valve to a full closed position;

turning said water faucet on;

inserting said brush head inside a mouth of said user;

operating said control valve between said full closed position and a full open position regulating the flow of water through said body and said holes;

brushing said teeth of said user;

controlling a rate of pulsation of said water expelled from said holes by rotating said control end of said braking mechanism in a first direction urging said pad end against said shoe end decreasing said rate of pulsation of said water, and by rotating said control end of said braking mechanism in a second direction urging said pad end away from said shoe end increasing said rate of pulsation of said water;

moving said control valve to said full closed position blocking the flow of said water through said body;

removing said brush head from said mouth;

turning said water faucet off; and disconnecting said second connector end of said flexible hose from said water faucet.

* * * * *